United States Patent [19]

Brannon et al.

[11] 3,932,619

[45] Jan. 13, 1976

[54] METABOLITE A-27106 AND PROCESSES FOR ITS PREPARATION AND USE

[75] Inventors: Donald R. Brannon, Pittsboro; Donald R. Horton, Brownsburg, both of Ind.

[73] Assignee: Eli Lilly and Company, Indianapolis, Ind.

[22] Filed: May 24, 1974

[21] Appl. No.: 473,016

Related U.S. Application Data

[63] Continuation-in-part of Ser. No. 328,586, Feb. 1, 1973, abandoned.

[52] U.S. Cl. ............................................... 424/120
[51] Int. Cl.² ........................................ A61K 35/00
[58] Field of Search ...................................... 424/120

[56] References Cited

UNITED STATES PATENTS 3,501,568   3/1970   Haney et al. ........................ 424/121

*Primary Examiner*—Jerome D. Goldberg
*Attorney, Agent, or Firm*—Nancy J. Harrison; Everet F. Smith

[57] ABSTRACT

Metabolite A-27106 sodium salt is obtained by reaction of monensin and glucose with an enzyme system produced by submerged aerobic culture of *S. candidus* NRRL 5449. Metabolite A-27106 and salts thereof are anticoccidial agents and also increase feed-utilization efficiency in ruminants.

3 Claims, 1 Drawing Figure

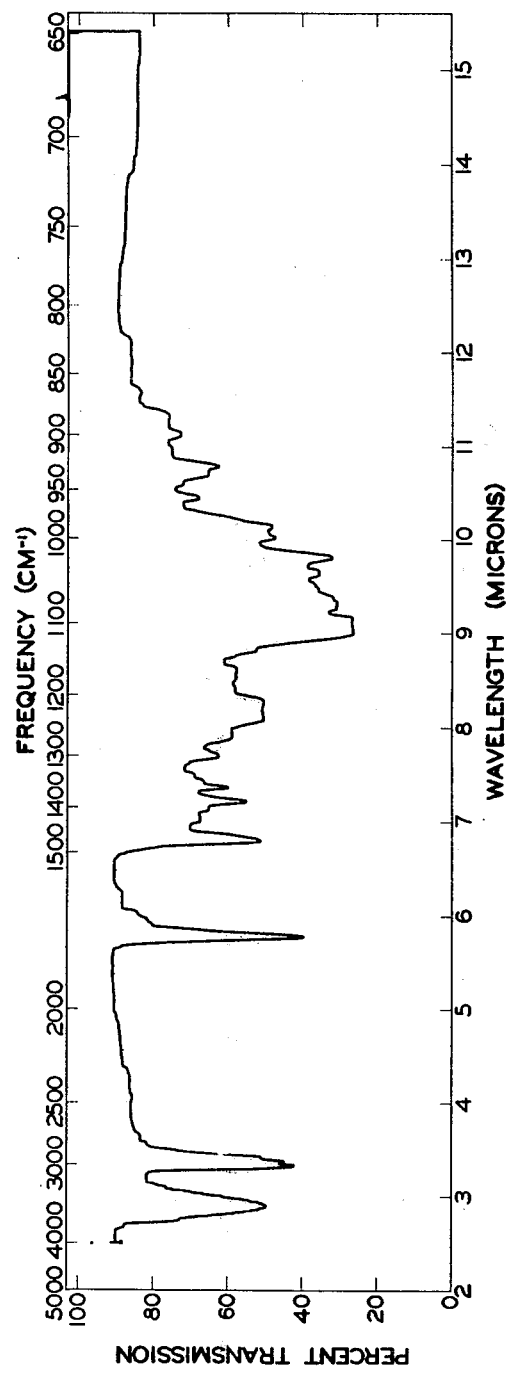

METABOLITE A-27106 AND PROCESSES FOR ITS PREPARATION AND USE

CROSS-REFERENCE TO RELATED APPLICATION

This is a continuation-in-part of my copending application Ser. No. 328,586, filed Feb. 1, 1973, now abandoned.

BACKGROUND OF THE INVENTION

1. Field of the Invention

The agent of this invention protects poultry from coccidiosis and benefits ruminants.

Coccidiosis is a well-known protozoan disease resulting from infection by one or more species of Eimeria or Isospora (for a summary, see Lund and Farr in "Diseases of Poultry" 5th ed., Biester and Schwarte, Eds., Iowa State University Press, Ames, Ia., pp 1056–1096). In view of the great economic losses from coccidiosis, the search for better anticoccidial agents continues.

Because ruminants are animals of economic importance, increasing ruminant feed-utilization efficiency is very desirable. The mechanism for utilization of the major nutritive portion (carbohydrates) of ruminant feed is well known. Microorganisms in the rumen of the animal ferment carbohydrates to produce monosaccharides and then degrade these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Ed., Oriel Press, pp 408–410.

The relative efficiency of utilization of the VFA's is discussed by McCullough, *Feedstuffs*, June 19, 1971, page 19; Eskeland et al., *Feedstuffs* An. Sci. 33, 282 (1971); and Church et al., "Digestive Physiology and Nutrition of Ruminants," Vol. 2, 1971, pp 622 and 625. Although acetates and butyrates are utilized, propionates are utilized with relatively better efficiency. Furthermore, when too little propionate is available, animals may develop ketosis. A beneficial drug, therefore, encourages animals to produce propionates from carbohydrates, thereby increasing carbohydrate-utilization efficiency and also reducing the incidence of ketosis.

2. The Prior Art

Monensin, from which metabolite A-27106 can be prepared, was disclosed in U.S. Pat. No. 3,501,568 as factor A of antibiotic A3823 complex. Monensin is also an anticoccidial agent.

SUMMARY OF THE INVENTION

This invention is related to novel compositions of matter, metabolite A-27106 and salts thereof, and to the process for the production thereof from monensin by an enzyme or enzymes (hereinafter referred to as an enzyme system) produced by the growth of a novel strain of *Streptomyces candidus* in a glucose-rich medium.

In accordance with the preparative procedures usually employed, metabolite A-27106 is isolated from fermentation broth as the crystalline sodium salt, using well-known methods, preferably by extraction with organic solvent and purification via chromatography. Metabolite A-27106 (the free acid) and the ammonium and other alkali-metal salts thereof are prepared by standard chemical procedures from the sodium salt.

Metabolite A-27106 and salts thereof are useful anticoccidial agents. Moreover, these compounds benefit ruminants by increasing feed-utilization efficiency and decreasing the incidence of ketosis.

The invention also relates to a method of protecting poultry which comprises administering a coccidiosis-inhibiting dose of metabolite A-27106 or a salt thereof to a bird susceptible to coccidiosis. The invention additionally relates to a feed adapted to carry said dose.

DESCRIPTION OF THE DRAWING

The infrared absorption spectrum in chloroform of metabolite A-27106 sodium salt is presented in the accompanying drawing.

DETAILED DESCRIPTION

The free-acid form of the biologically active agent of this invention is arbitrarily designated as metabolite A-27106. The sodium, lithium, potassium, rubidium, cesium and ammonium salts of metabolite A-27106 are also biologically active and are part of this invention. For the sake of brevity, the term "A-27106 compound" is used generally in the specification and refers to either the free acid or one of the specified salts.

A starting material in the preparation of metabolite A-27106 is monensin, the sodium salt of which has the formula

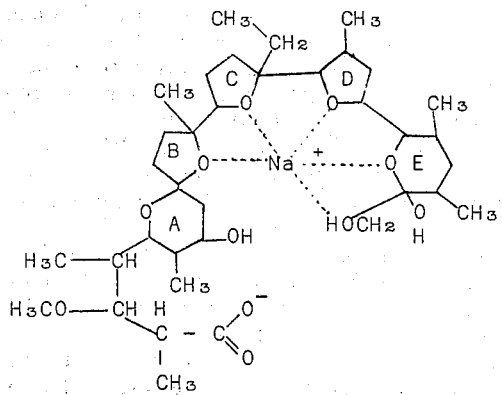

Monensin in its sodium form is obtained from *Streptomyces cinnamonensis* as described in U.S. Pat. No. 3,501,568. For convenience, the term monensin is used throughout this specification. As will be recognized by those skilled in the art, however, the term monensin can refer to monensin in either the free acid or salt form. The common form of monensin is, in general, the sodium salt.

Metabolite A-27106 is produced from either monensin or the mycelial culture in which monensin is produced, in the presence of glucose, by an enzyme system produced by a new strain of *Streptomyces candidus*. A culture of this new strain has been deposited, without restriction as to availability, with the permanent culture collection of the Northern Utilization Research and Development Division, Agricultural Research Service, United States Department of Agriculture, 1815 North University St., Peoria, Ill. 61604, where it was assigned the accession number NRRL 5449.

Because of the uncertainty of taxonomic studies with the Streptomyces group of organisms, there is always an element of doubt associated with the classification of a newly discovered organism. In the most important characteristics, however, organism NRRL 5449 which converts monensin into metabolite A-27106 appears to resemble most nearly *Streptomyces candidus* (Krassilnikov) Waksman 1953. The type culture is described by S. A. Waksman in "The Actinomycetes," Vol. II, Williams and Wilkins, Baltimore, 1961, p. 187. The type organism is also on deposit at the Institute of Microbiology of Rutgers University, New Brunswick, N.J., under the accession number IMRU 3416. The present organism is considered a novel strain of the described organism. Although *S. candidus* NRRL 5449 and the known strain resemble one another in general mycelial morphology and color and in spore appearance, sufficient differences exist between them to require that the organism described in the present invention be characterized as a new strain. For example, the published organism does not coagulate milk and liquifies gelatin slowly, whereas the new strain forms curd after 14 days and does not liquefy gelatin in 21 days. Most importantly, a specimen culture propagated from strain IMRU 3416 did not convert monensin to metabolite A-27106.

The organism which converts monensin into metabolite A-27106 was isolated from a soil sample collected on Mount Ararat, Turkey, by suspending portions of the soil in sterile distilled water and streaking the suspension on nutrient agar. The seeded agar plates were incubated at 25°–35°C. until visible colonies were observed. At the end of the incubation period, colonies of selected organisms were transferred by means of a sterile platinum loop to agar slants. One of the slants was then incubated to provide suitable quantities of inoculum of organism NRRL 5449.

Taxonomic studies of *S. candidus* NRRL 5449 were made using methods recommended for the International Cooperative Project for Description and Deposition of Streptomycetes in accordance with procedures described by Shirling and Gottlieb, "Methods for Characterization of Streptomyces Species," *International Bulletin of Systematic Bacteriology* 16, 313–340 (1966), together with other supplementary tests. The prefix "ICP" refers to media described by Shirling and Gottlieb. The remaining media are described by Waksman, cited. Color names were assigned according to Kelly and Judd in "The ISCC-NBS Method of Designating Colors and Dictionary Dictionary of Color Names," U.S. Department of Commerce circular 533, 1955. Figures in parenthesis refer to the Tresner and Backus color series, "System of Color Wheels for Streptomyces Taxonomy," *Appl. Microbiol.* 11, 335 (1963). Color tab designations are underlined, and Maerz and Paul ("Dictionary of Color," McGraw-Hill N.Y., 1950) color blocks are enclosed in brackets.

Microscopic Morphology

Streptomycete NRRL 5449 is characterized by straight to wavy sporophores and oval to slightly cylindrical spores, averaging $1.16\mu \times 0.57\mu$, in chains of from 10 to 50. Spores are smooth as observed by electron microscopy. Aerial mycelia are usually white. At 26°C. only vegetative growth occurs, and at 45°C. no growth occurs. Maximum growth and sporulation occur at 30° to 37°C.

Cultural Characteristics

In accordance with standard practice, the growth of microorganism NRRL 5449 was studied on a variety of media that are accepted in the study of the Actinomycetes. Cultural procedures were uniform and standard. The media employed and the cultural characteristics observed are set forth below:

ICP 1 Fair growth; pale yellow reverse [11C1]; no aerial mycelia or spores; no soluble pigment.

ICP 2 Abundant growth; reverse light yellow [10J3]; abundant aerial mycelia and spores; (W) white *a*; no soluble pigment.

ICP 3 Good growth; reverse pale yellow green [10C1]; good aerial mycelia and spores; (W) white *a*; no soluble pigment.

ICP 4 Good to abundant growth; reverse moderate yellow [10H4]; good to abundant aerial mycelia and spores; (W) white *a*; brown soluble pigment.

ICP 5 Abundant growth; reverse moderate orange yellow [10I6]; abundant aerial mycelia and spores; (Y) pale yellow 2*db*; slight brown soluble pigment.

ICP 7 Good growth; reverse pale yellow green [10B1]; good aerial mycelia and spores; (W) white *a*; no soluble pigment.

Glycerol-Glycine Abundant growth; medium brown reverse [11J4]; abundant sporulation and aerial mycelia; (W) white a and (Y) pale yellow 2*db*; slight light brown soluble pigment.

Emerson's Abundant growth; grayish yellow reverse [12H3]; no aerial mycelia or spores; no soluble pigment.

Bennett's Good growth; light yellow reverse [11I2]; scant aerial mycelia and spores; (W) white *a*; no soluble pigment.

Czapek's Abundant growth; moderate orange yellow [11J7]; abundant aerial mycelia and spores; (W) white *a*; no soluble pigment.

Glucose-Asparagine Fair to good growth; pale yellow green reverse [10B1] no aerial mycelia or spores; no soluble pigment.

Calcium malate Abundant growth; reverse grayish yellow [11E4]; abundant aerial mycelia and spores; (Y) pale yellow 2ba; slight brown soluble pigment.

Nutrient Agar Good growth; reverse pale yellow green [10C1]; no aerial mycelia or spores; no soluble pigment.

The organism was studied for selected physiological properties in accordance with standard procedures. The properties observed and characteristics found were as follows:

| Property Observed | Characteristic |
|---|---|
| Action on skim milk | clearing; curd after 14 days |
| Nitrate reduction | positive |
| Melanin production | |
| Tryptone yeast extract broth | slight |
| Tyrosine agar | none |
| Gelatin liquefaction | none at 21 days |
| Temperature requirements | 26°C.—vegetative growth only |
| | 30–37°C.—good vegetative growth; good aerial mycelia and spores |
| | 43–55°C.—no growth |

The results of carbon utilization tests carried out with organism NRRL 5449 are set forth below. The symbols used to indicate growth response are:

+ = Utilization — good growth
[+] = Probable utilization — poor to fair growth
[−] = Questionable utilization — little or no growth
− = No utilization — no growth.

| Carbon source | Response |
| --- | --- |
| raffinose | + |
| D-fructose | [+] |
| cellobiose | [+] |
| L-arabinose | [+] |
| D-mannitol | [+] |
| rhamnose | [+] |
| cellulose | − |
| dextrose | [+] to [−] |
| D-xylose | [+] |
| inositol | + |
| −C (no carbohydrate) | [−] to [+] |

Requirements for Optimum Growth

The culture medium employed to grow S. candidus NRRL 5449 can be any one of a number of media. However, for economy in production, optimal yield, and ease of product isolation, certain culture media are preferred. Thus, for example, among the preferred sources of carbohydrate in large-scale fermentation are invert sugar or corn syrup, although glucose, fructose, maltose, starch, inositol, and the like can also be employed. When monensin is to be converted to metabolite A-27106 in fermentation culture at the time S. candidus NRRL 5449 is grown, the medium must contain a source of glucose to achieve efficient conversion. When S. candidus NRRL 5449 is grown to produce its enzyme system for later use in converting monensin to metabolite A-27106, the presence of glucose during fermentation is optional. Preferred sources of nitrogen are peptones, soybean meal, amino acid mixtures and the like. Among the nutrient inorganic salts which can be incorporated in the culture media are the customary soluble salts capable of yielding iron, sodium potassium, ammonium, calcium, phosphate, chloride, carbonate, and like ions.

Essential trace elements necessary for the growth and development of the organism should also be included in the culture medium. Such trace elements commonly occur as impurities in other constituents of the medium in amounts sufficient to meet the growth requirements of the organism.

The initial pH of the culture medium can be varied. Prior to inoculation with the organism, however, it is desirable to adjust the pH of the culture medium to between about pH 5.7 and about pH 7.5, depending upon the particular medium employed. As is the case with other Actinomycetes, the medium gradually becomes more alkaline as the fermentation proceeds and may rise from an initial pH of about pH 5.9 to about pH 6.9 or higher during the growth period of the organism. The final pH is controlled, at least in part, by the initial pH of the medium, the buffers present in the medium, and the duration of time the organism is permitted to grow. Although pH can be adjusted by addition of either acid or base, good results have been achieved with no adjustment of pH.

In common with other Streptomyces species, organism NRRL 5449 requires aerobic growth conditions. Small-volume propagation is conveniently carried out on agar slants or plates, in shake flasks or in bottles. For large-scale production, submerged aerobic culture in large tanks is preferred.

The fermentation medium in a sterile tank can be inoculated with a sporulated suspension to initiate fermentation. However, since inoculation with a sporulated suspension involves a growth lag, a vegetative inoculum is preferable. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that used for large-scale production, but other media can be employed.

The organism S. candidus NRRL 5449 will grow over a temperature range between about 26°C. to about 40°C. Maximum growth and sporulation, however, occur between about 32°C. and about 37°C.

As is customary in aerobic submerged culture processes, sterile air is blown through the culture medium during fermentation. For efficient growth of the organism and production of metabolite A-27106, the volume of air employed in tank production of the substance should be above about 0.1 volume of air per volume of culture medium per minute. Optimal yields are obtained when the volume of air used is at least one-third to one-half volume of air per volume of culture medium per minute.

The fermentation time needed to convert monensin to metabolite A-27106 varies. The presence of an adequate supply of glucose is essential for the conversion of monensin to metabolite A-27106. In general, when glucose is present in adequate amounts and monensin is present in about 0.1 to 1.0 grams per liter of medium, conversion of monensin to metabolite A-27106 is essentially complete by about 36 to 72 hours. Optimal conversion occurs when monensin is present in a range of from 0.5 to 0.7 grams per liter of medium. An adequate amount of glucose is above 2 percent of medium by weight. A preferred amount of glucose is from about 2.0 to about 2.5 percent of medium by weight. A glucose-sensing test paper may be used to check concentration levels. When glucose content drops below about two percent, glucose should be added to maintain concentration at optimum levels.

When the separated S. candidus enzyme system is used to effect conversion of monensin to metabolite A-27106, it is not essential that the enzyme preparation be highly purified. For example, filtered fermentation broth can be lyophilized and stored for at least as long as two weeks before reconstituting with an aqueous buffer, using approximately one-sixth the volume of original broth. Efficient conversion is achieved after about 72 hours when 2.5 g. of such a lyophilized preparation is reconstituted in the presence of 25 mg. of monensin.

The active enzyme system is present in both the filtered broth and the cells. An enzyme system of greater purity can be obtained from the separated fermentation cells. These cells may be frozen and stored for periods at least as long as three months. The thawed cells can be then reconstituted by suspending them in a buffer solution. The buffer suspension is further purified by sonication and centrifugation. The purified cell debris thus separated is resuspended in buffer and is dialyzed. Using this method, 200 g. of cells from the fermentation medium give purified dialyzate sufficient to convert glucose and 25 mg. of monensin to metabolite A-27106.

Detection and Assay

Conversion progress can be monitored by thin-layer chromatography (tlc). On silica gel (F-254, E-N Laboratories, Inc., Elmsford, N.Y.) in benzene-methanol (7:3), the Rf value for monensin is 0.62, whereas the Rf value for metabolite A-27106 sodium salt is 0.49. A vanillin spray reagent can be used for detection. This reagent is prepared by adding fuming sulfuric acid (2 ml.) to a solution of vanillin (3 g.) in absolute ethanol (100 ml.).

Isolation

Metabolite A-27106 is present in both the culture broth and in the mycelia. Accordingly, techniques employed in the isolation of the metabolite are designed to permit maximum recovery of the product from either or both sources. Thus, for example, the fermentation medium is filtered, and both the filtrate and the mycelial cake are extracted with suitable solvents to obtain metabolite A-27106 as the sodium salt. The product is recovered from the extracting solvents by ordinary methods commonly employed in the art.

Alternatively, the culture solids, including medium constituents and mycelia, can be used without extraction or separation, but preferably with removal of water from the mycelia and culture medium, as a source of metabolite A-27106 sodium salt. For example, the culture medium can be dried by lyophilization and mixed into feed. Also, the solids can be converted without total removal of water to a thin slurry which is suitable for addition to wet mash and similar feeds.

No single extraction/isolation procedure is mandatory. In one satisfactory manner, the finished culture medium is filtered, using a filter aid. The filter cake is extracted with a polar solvent such as methanol. The methanol extract is concentrated and then added to the original aqueous filtrate. This combined solution is extracted twice with half volumes of chloroform. The chloroform extracts are evaporated under vacuum to give a dark amber oil.

This oil is decolorized over an activated-charcoal column, using chloroform and about 20 g. of activated charcoal per gram of oil. The elute is again concentrated under vacuum to give a pale yellow to colorless oil. This oil, dissolved in a minimal amount of chloroform, is chromatographed on a silica-gel column, using ethyl acetate as a solvent. Elution is monitored by thin-layer chromatography. Impurities are eluted with ethyl acetate. Elution with ethyl acetate-methanol mixtures affords metabolite A-27106 sodium salt.

Characteristics of A-27106

Metabolite A-27106 sodium salt is a white crystalline solid, melting with bubbling at about 170°–175°C. Metabolite A-27106 sodium salt appears to form a hydrate or other solvate very readily. When A-27106 sodium salt is hydrated or solvated, its melting point varies, generally melting a few degrees below the indicated value.

Elemental analysis of metabolite A-27106 sodium salt gave the following percentage composition: carbon, 58.78; hydrogen, 8.51; oxygen, 27.85; and sodium, 3.63. These values correlate with empirical formula $C_{42}H_{71}O_{16}Na$ which has a theoretical percentage composition of carbon, 59.00; hydrogen, 8.37; oxygen, 29.94; and sodium, 2.42.

Metabolite A-27106 sodium salt exhibits practically no ultraviolet absorption above about $235\mu$.

The infrared absorption spectrum of metabolite A-27106 sodium salt in chloroform is shown in FIG. 1 of the accompanying drawing. The distinguishable absorption maxima of the spectrum are as follows: 3.1, 3.36, 6.39, 6.82, 7.1, 7.25, 7.9 (shoulder), 8.1, 8.3, 8.67, 8.8 (shoulder), 9.04, 9.22, 9.51, 9.66, 10.03, 10.26, 10.66, 11.23, 11.47, 11.83, and 12.15.

The mass spectrum of metabolite A-27106 sodium salt shows a molecular-ion peak and other characteristic peaks as listed below:

| m/e | | |
|---|---|---|
| Calcd. | Observed | Fragment |
| 854.46230 | 854.44630 | $C_{42}H_{71}O_{16}Na$ $(M^+)$ |
| 836.45229 | 836.44129 | $C_{42}H_{69}O_{15}Na$ $(M^+ - H_2O)$ |
| 779.45490 | 779.44690 | $C_{40}H_{68}O_{13}Na$ $(M^+ - [CH_3O. + CO_2])$ |
| 761.44540 | 761.44740 | $C_{40}H_{66}O_{12}Na$ $(M^+ - [CH_3O. + CO_2 + H_2O])$ |

These findings confirm the assigned empirical formula and a molecular weight of 854 for metabolite A-27106 sodium salt.

In general, metabolite A-27106 sodium salt is readily soluble in highly polar solvents, is insoluble in nonpolar solvents, and varies in solubility in solvents of intermediate polarity. Illustratively, A-27106 sodium salt is soluble in lower aliphatic alcohols, is partially soluble in phenol, diethyl ether and acetone, and is relatively insoluble in liquid lower alkanes.

The acid form of metabolite A-27106 is a white amorphous solid, having a molecular weight of about 832. Electrometric titration of metabolite A-27106 (free acid) in water at an initial pH of 8 revealed the presence of a titratable group with a pKa value of 7.2.

The monosodium salt is, in general, the natural form of metabolite A-27106. From the sodium salt, the free acid is easily produced; from the free acid, the ammonium and other alkali-metal salts are prepared. The various metallic salts behave somewhat like alkali-metal carboxylates and somewhat like chelates.

In preparing another form, metabolite A-27106 sodium salt is dissolved in an aqueous solvent, such as methanol-water; an acid such as, for example, hydrochloric acid is added to lower the pH to 5 or below. The methanol is removed under vacuum, and the resulting aqueous acid product is extracted with chloroform. The chloroform extract is dried and evaporated to give metabolite A-27106, the free acid.

The free-acid form of metabolite A-27106 can be further modified by titrating it with an aqueous alkali-metal hydroxide or aqueous ammonia to obtain the corresponding lithium, potassium, rubidium, cesium or ammonium forms. Metabolite A-27106 and the ammonium and alkali-metal salts thereof are all biologically active.

The exact structure of metabolite A-27106 is not known. It is known that, in the conversion of monensin to metabolite A-27106, glucose is necessary and is consumed, even in the absence of metabolizing *S. candidus* cells. The molecular weight of A-27106 corresponds to that of a glucosyl monensin.

Other than the highly hindered tertiary hydroxyl on the E ring, there would be five hydroxyl sites on a glucosyl monensin, any or all of which should be susceptible of reaction to form a simple ester such as an acetate. The presence of all five such reactive sites has been demonstrated in esterification experiments.

Based on the physical characteristics hereinabove recited, the following structure can be proposed for metabolite A-27106 sodium salt:

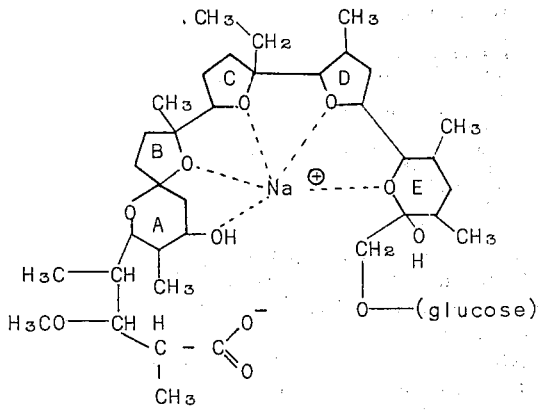

Since the structure is only postulated, it is to be understood that the structure presented above represents merely a working hypothesis.

Metabolite A-27106 is less toxic than monensin. In tests when metabolite A-27106 sodium salt was administered intraperitoneally to groups of six mice each:

at 50 mg./kg. one out of six died;
at 100 mg./kg. three out of six died.
In similar tests, when monensin sodium salt was administered intraperitoneally to groups of six mice each:

at 10 mg./kg. one out of six died;
at 20 mg./kg. three out of six died.

For the prevention or treatment of coccidiosis in poultry, a non-toxic, anticoccidial amount of an A-27106 compound is administered to birds, preferably orally on a daily basis. Although a variety of factors must be considered in determining an appropriate concentration of an A-27106 compound, the rate of administration will be generally in the range of 0.005 to 0.05 percent by weight of unmedicated feed, and preferably in the range of 0.01 to 0.04 percent. An A-27106 compound can be supplied in many ways, but it is most conveniently supplied with a physiologically-acceptable carrier, preferably the feed ingested by the birds.

A-27106 compounds also improve feed utilization in ruminants which have a developed rumen function. Young ruminants, basically those still unweaned, function as monogastric animals. As young ruminants begin to eat solid food, the rumen function begins to develop, and the microbiological population of the rumen begins to increase. After the animal has eaten solid feed for a time, its rumen function reaches full development and continues to operate throughout the animal's life. Some economically important ruminant animals are cattle, sheep and goats.

An A-27106 compound is typically effective in increasing the efficiency of feed-utilization when administered to ruminants orally at rates of from about 0.05 mg./kg./day to about 2.5 mg./kg./day. Most beneficial results are achieved at rates of from about 0.1 mg./kg./day to about 1.5 mg./kg./day. A preferred method of administration of an A-27106 compound is by mixing it with the animals' feed; however, it can be administered in other ways, for example, tablets, drenches, boluses, or capsules. Formulation of these various dosage forms can be accomplished by methods well known in the veterinary pharmaceutical art. Each individual dosage unit should contain a quantity of an A-27106 compound directly related to the proper daily dose for the animal to be treated.

In order to more fully illustrate the methods and procedures of the present invention, the following examples are provided.

EXAMPLE 1

Preparation of A-27106 from Monensin by *S. candidus*

*S. candidus* NRRL 5449 was grown on an agar slant prepared from Bennett's medium to give a well-defined colony. The colony was removed and made up as a slurry with sterile deionized water (10 ml.).

This slurry was divided among four 500-ml. shake flasks, each containing 100 ml. of vegetative medium of the following composition:

| Ingredient | Amount |
|---|---|
| Corn distillers' solubles* | 25. g. |
| Lactose | 10. g. |
| Maltose | 10. g. |
| $FeSO_4.7H_2O$ | 0.01 g. |
| $MgSO_4.7H_2O$ | 2. g. |
| $KH_2PO_4$ | 2. g. |
| $CaCO_3$ | 2. g. |
| Deionized water | q.s. 1.1 liter |

*Nadrisol, National Distiller's Products Company

The four inoculated flasks were incubated at 30°C. on a rotary shaker at 250 r.p.m. for 24 hours. This vegetative medium (10-ml. portions) was used to inoculate each of 15 shake flasks (500 ml.) containing 100 ml. of sterilized fermentation medium of the following composition:

| Ingredient | Amount |
|---|---|
| Beef extract | 5 g. |
| Casein pancreatic hydrolysate peptone | 5 g. |
| NaCl | 5 g. |
| Glycerol | 15 g. |
| $CaCO_3$ | 2 g. |
| Deionized water | q.s. 1 liter |

The medium had a pH of 7.2 which was not adjusted. The inoculated medium was incubated for 72 hours as described above.

In a 40-liter fermentor a production medium of the following composition was prepared:

| Ingredient | Amount |
|---|---|
| Polysiloxane oil antifoam agent | 5 g. |
| Glycerol | 375 g. |
| Dextrose | 625 g. |
| Casein pancreatic hydrolysate peptone | 125 g. |
| Beef extract | 125 g. |
| NaCl | 125 g. |
| $CaCO_3$ | 50 g. |
| Deionized water | q.s. 24 liters |

The initial pH of the medium was 7.0. The medium was then sterilized by autoclaving at 120°C. for 30 minutes at 15–20 pounds per square inch pressure. After sterilization, the pH of the medium was 7.6.

Purified monensin (25 g.) dissolved in ethanol (200 ml.) was added to the sterilized medium, and the second-stage vegetative inoculum (700 ml.) prepared as described above was introduced.

The fermentation medium was aerated with sterile air at a rate of 0.5 volume of air per volume of medium per minute (v./v./m.) and was stirred with conventional agitators at 420 r.p.m. The inoculated medium was incubated at 30°C. for about 114 hours.

The course of the fermentation was followed by thin-layer chromatography on silica gel as described hereinabove. Early in the fermentation only monensin was present. Gradually a second spot indicated the presence of metabolite A-27106 sodium salt; and finally, only the spot for metabolite A-27106 sodium salt was present.

EXAMPLE 2

Isolation and Purification of A-27106 Sodium Salt

The fermentation broth, prepared as described in Example 1, was filtered, using a filter aid. The mycelial cake was extracted with methanol (about 5 l.) at room temperature. The methanol extract was filtered; the filtrate was concentrated under vacuum, removing the methanol and leaving an aqueous concentrate.

This aqueous concentrate was combined with the original broth filtrate. The combined solution (about 22 l.) was extracted twice with half-volumes of chloroform. The chloroform extracts were combined and concentrated under vacuum to about 400 ml. of a dark amber oil.

This oil, dissolved in chloroform, was decolorized over a 10-kg. carbon (Pittsburg "12 X 40") column, eluting with chloroform (about 5 l.). The chloroform eluate was evaporated under vacuum to give about 500 ml. of a colorless to pale-yellow oil.

The decolorized oil, in a minimal amount of chloroform, was then chromatographed over a 25-kg. column of silica gel (Grace, grade 62) in ethyl acetate. Elution was monitored by thin-layer chromatography as described earlier. After impurities were removed with ethyl acetate, the product was eluted from the column with ethyl acetate-methanol (19:1). The fractions containing the product were combined and evaporated to dryness under vacuum to give an amorphous, almost white product. The product was washed with hexane and dried to give about 12.84 g. of metabolite A-27106 sodium salt (one-spot material by tlc).

EXAMPLE 3

Production of A-27106 by S. cinnamonensis and S. candidus.

Another method of producing metabolite A-27106 in fermentor culture is illustrated by the following procedure:

*Streptomyces cinnamonensis* ATCC 15413 was conventionally grown (see U.S. Pat. 3,501,568) in 55 ml. of medium in a 250-ml. shake flask, incubating for 47 hours to obtain a vegetative inoculum. This vegetative inoculum was added to 220 ml. of medium in a one-liter shake flask and was incubated for 21 hours to supply inoculum for seeding the fermentor.

The inoculum thus prepared was used to seed a 40-l. fermentor containing a heat-sterilized medium of the following composition:

| Ingredient | Amount |
| --- | --- |
| Glucose | 750.0 g. |
| Soybean meal | 625.0 g. |
| Soybean oil | 500.0 g. |
| Methyl oleate | 500.0 g. |
| Polysiloxane oil antifoam | 5.0 g. |
| Potassium chloride | 2.5 g. |
| Dipotassium hydrogen phosphate | 2.5 g. |
| Manganous chloride tetrahydrate | 15.0 g. |
| Hydrated ferric sulfate | 7.5 g. |
| Calcium carbonate | 25.0 g. |
| Deionized water | q.s. 24 liters |

The resulting medium had a pH of 5.5 which was adjusted to pH 8.0 by addition of 10 N potassium hydroxide (15 ml.). The inoculated medium was incubated at 32°C. for 234 hours.

After 42 hours, aeration was increased from 0.5 to 1.1 v./v./m., and agitation was increased from 500 to 700 r.p.m. Monensin production was essentially complete after 210 hours, as determined by thin-layer bioassay with *Bacillus subtilis* ATCC 6633 as the detection organism.

After 234 hours, the fermentor contents were pasteurized to inactivate *S. cinnamonensis*. The following nutrients were then added to the fermentor:

| Ingredient | Amount | |
| --- | --- | --- |
| Dextrose | 750 | g. |
| Soybean meal | 625 | g. |
| Manganous chloride tetrahydrate | 15 | g. |
| Calcium carbonate | 12.5 | g. |
| Ferric sulfate hexahydrate | 7.5 | g. |
| Potassium chloride | 2.5 | g. |
| Dipotassium hydrogen phosphate | 2.5 | g. |
| Methyl oleate | 250 | ml. |
| Soybean oil | 250 | ml. |
| Deionized water | q.s. 24 liters | |

The pH was adjusted to 8.0 with 215 ml. of 5 N NaOH, and the medium was sterilized. The medium was then inoculated with a rapidly growing vegetative culture of *Streptomyces candidus* NRRL 5449 and was incubated for 137 hours at 30°C. The fermentation was aerated with sterile air at a rate of 0.5 v./v./m. The fermentation medium was stirred with conventional agitators first at 120 r.p.m., increasing after 16 hours to 420 r.p.m. and after 40 hours to 500 r.p.m. Dextrose (400 g.) was added at each of hours 44, 66.5, 89, 97, 113, and 127. Calcium carbonate (175 g.) was added at each of hours 72 and 99.

Thin-layer chromatography as described hereinabove was used to monitor the fermentation. After 137 hours production of metabolite A-27106 was essentially complete. Work-up and purification of A-27106 sodium salt followed the procedures described in Example 2.

EXAMPLE 4

Production of A-27106 by a Particulate *S. candidus* Enzyme System

*S. candidus* NRRL 5449 was grown as described in Example 1, on a 100-liter scale. The cells were separated from the fermentation medium by vacuum filtration and were divided into 200-g. aliquots which were stored by freezing. Two of these aliquots were thawed at room temperature and were suspended in 0.05 M phosphate buffer (pH 5.8) to a final volume of 600 ml. This cell suspension was sonicated for 30 minutes, and the sonicate was centrifuged at 10,000 rpm for 30 minutes. The resulting cell debris was suspended in 100 ml. of the above-mentioned buffer; this suspension was dialyzed for 18 hours with 5 l. of chilled, above-mentioned buffer. To 50 ml. of the particulate dialyzed enzyme were added D-glucose (120 mg.) and monensin (25 mg.) in ethanol (2 ml.). The reaction mixture was stirred for 72 hours at 30°C. and then was filtered; the filtrate was extracted with chloroform (100 ml.). This chloroform extract, concentrated under vacuum, was chromatographed on a silica gel column (10 g.). Elution with ethyl acetate gave only a trace of monensin. Elution with ethyl acetate-methanol (19:1) gave 17 mg. of metabolite A-27106 sodium salt, identical to that obtained in Example 2.

EXAMPLE 5

Control of Coccidiosis with A-27106

A group of 75 one-week-old, healthy, incubator and battery-reared, cross-bred male chicks, of a heavy broiler type was used. The birds were divided into five groups of 15 birds having three replicates of five-bird subgroups each. Each subgroup was reared out of contact with the other subgroups. A first group was held as an untreated healthy control under favorable conditions. A second group was treated as the first group, but was inoculated with coccidiosis by oral administration of a dose containing $10^5$ sporulated oocysts of *Eimeria tenella*. The third, fourth and fifth groups were treated as the second group except that, 24 hours before the said inoculation, their feed was modified by addition of metabolite A-27106 sodium salt in concentrations of 100, 150, and 200 parts per million (ppm), respectively.

Seven days after inoculation, the birds were weighed, sacrificed and examined for evidence of coccidial lesions. Coccidial involvement was expressed on an arbitrary scale of zero to four. Lesion scores indicate the number of birds at each level. Zero indicates no evidence of coccidiosis. One designates the least coccidial involvement that can be seen. Two indicates moderate involvement with little or no hemorrhage and no severe tissue damage. Three indicates hemorrhage, swelling of the caeca, and extensive tissue involvement. Four indicates hemorrhage, a caecal core of clotted blood and debrided epithelial cells. Birds scoring four or less usually recover if not further infected with coccidia.

Using the above-described procedures, the following results were observed:

In the medicated birds with high lesion scores, fecal blood was scanty or absent, and the birds appeared to be in good condition. Their good weight gain was regarded as more meaningful than the lesion scores.

Since studies indicate that an A-27106 compound usually kills *E. tenella* as it first attempts to establish itself in the host cell, a prophylactic regimen of treatment is preferable.

In other studies metabolite A-27106 sodium salt was found to be more palatable to birds and also less toxic than was monensin.

Numerous other studies were carried out with metabolite A-27106 sodium salt, both alone and in combination with monensin. These studies showed that although A-27106 gave no greater weight gains at 0.04 percent than at 0.01 percent, the higher rate resulted in fewer caecal lesions. There was no evidence of toxicity at the higher rate.

Within the general efficacy range, monensin and metabolite A-27106 sodium salt combined in the diet show at least an additive result in efficacy, but not in toxicity. Toxicity of the combination is lower than that of monensin alone at a rate equal to the combined rates.

EXAMPLE 6

A-27106-Modified Chick Ration for Coccidiosis Control

A balanced, high-energy ration adapted to feed chicks for rapid weight gain is prepared by the following recipe:

| Ingredient | % | lbs. |
|---|---|---|
| Ground yellow corn | 50 | 1,000 |
| Soybean meal, solvent extracted dehulled, finely ground, 50 percent protein | 31.08 | 621.6 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A,D,E,K, and $B_{12}$, choline, niacin, pantothenic acid, riboflavin, biotin, with glucose bulking agent) | 0.5 | 10 |
| Trace mineral premix (representing $MnSO_4$, ZnO, KI, $FeSO_4$, $CaCO_3$) | 0.2 | 4 |
| 2-Amino-4-hydroxybutyric acid (Hydroxy analog of methionine) | 0.1 | 2 |
| Metabolite A-27106 sodium salt | 0.02 | 0.4 |

These substances are mixed in accordance with standard feed-mixing techniques. Chicks fed such a ration, with water ad libitum, are protected from exposure to coccidiosis; weight gains are comparable to those of coccidiosis-free chicks fed a similar, unmedicated diet.

| Group of Birds | Inoculated with *E. tenella* | A-27106 Sodium Salt (ppm) in the diet | Avg. Wt. Gain/Bird in Grams | Lesion Scores 0 | 1 | 2 | 3 | 4 |
|---|---|---|---|---|---|---|---|---|
| 1 | no | 0 | 162 | 15 | 0 | 0 | 0 | 0 |
| 2 | yes | 0 | 67 | 0 | 0 | 0 | 0 | 15 |
| 3 | yes | 100 | 157 | 4 | 1 | 0 | 3 | 7 |
| 4 | yes | 150 | 150 | 3 | 3 | 1 | 1 | 7 |
| 5 | yes | 200 | 166 | 5 | 0 | 0 | 0 | 10 |

EXAMPLE 7

Feed-Utilization Efficiency Improved by A-27106

Rumen fluid is obtained from a steer with a surgically-installed fistula opening into the rumen. The steer is maintained on a high-grain ration, the composition of which follows:

| | |
|---|---|
| 69.95% | coarse ground corn |
| 10 % | ground corncobs |
| 8 % | soybean meal (50% protein) |
| 5 % | alfalfa meal |
| 5 % | molasses |
| 0.6 % | urea |
| 0.5 % | dicalcium phosphate |
| 0.5 % | calcium carbonate |
| 0.3 % | salt |
| 0.07% | vitamin A and $D_2$ premix* |
| 0.05% | vitamin E premix** |
| 0.03% | trace mineral premix*** |

*Containing per pound: 2,000,000 I.U. of vitamin A; 227,200 I.U. of vitamin $D_2$ and 385.7 g. of soybean feed with 1% oil added
**Corn distillers dried grains with solubles containing 20,000 I.U. of d-alpha tocopheryl acetate per pound
***Containing manganous oxide, potassium iodide, cobalt carbonate, copper oxide and zinc sulfate A sample of rumen fluid is strained through four layers of cheesecloth, and the filtrate is collected. The particulate matter retained by the cheesecloth is resuspended in enough physiological buffer to return it to the original volume of the rumen fluid, and this suspension is strained again. The buffer used has the following composition:

| g./liter | Ingredient |
|---|---|
| 0.316 | $Na_2HPO_4$ |
| 0.152 | $KH_2PO_4$ |
| 2.260 | $NaHCO_3$ |
| 0.375 | KCl |
| 0.375 | NaCl |
| 0.112 | $MgSO_4$ |
| 0.050 | $CaCl_2 \cdot 2H_2O$ |
| 0.008 | $FeSO_4 \cdot 7H_2O$ |
| 0.004 | $MnSO_4 \cdot H_2O$ |
| 0.004 | $ZnSO_4 \cdot 7H_2O$ |
| 0.002 | $CuSO_4 \cdot 5H_2O$ |
| 0.001 | $CoCl_2 \cdot 6H_2O$ | as described by Cheng et al., in *J. Dairy Sci.* 38, 1225–1230, (1955).

The two filtrates are combined and allowed to stand until particulate matter separates to the top. The clear layer is separated, diluted with the same buffer (1:1) and then adjusted to pH 7.0.

The diluted rumen fluid (10 ml.) is placed in a 25-ml. flask with 40 mg. of the above-described feed, an additional 5 mg. of soybean protein, and the compound to be tested. Four replicate flasks are used per treatment. Two sets of four control flasks each are also employed. A zero-time control and an incubated 16-hour control are used. All test flasks are incubated for 16 hours at 38°C. After incubation the pH is measured, and 25 percent metaphosphoric acid (2 ml.) is added to each flask. The samples are allowed to settle, and the supernatant is analyzed by gas chromatography for propionate, acetate, and butyrate compounds. Active compounds significantly increase propionate production over that of controls.

Test-compound results are statistically compared with the control results. The table below shows the ratio of volatile-fatty-acid concentrations in A-27106 (sodium salt)-treated flasks to concentrations in control flasks.

| mcg. A-27106/ml. diluted rumen fluid | Propionate | Butyrate | Total VFA |
|---|---|---|---|
| 5 | 2.15 | 0.73 | 1.03 |
| 1 | 1.42 | 0.96 | 0.98 |
| 0.2 | 1.02 | 0.91 | 1.07 |

EXAMPLE 8

A-27106-Improved Beef-Cattle Ration

A balanced high-grain beef-cattle ration is prepared as follows:

| Ingredient | Percent | Pounds Per Ton |
|---|---|---|
| Finely ground corn | 67.8 | 1356 |
| Ground corn cob | 10 | 200 |
| Dehydrated alfalfa meal, 17 percent protein | 5 | 100 |
| Dehulled soybean meal, solvent extracted, 50 percent protein | 9.9956 | 199.912 |
| Cane molasses | 5 | 100 |
| Urea | 0.6 | 12 |
| A-27106 Sodium Salt | 0.0044 | .088 |
| Dicalcium phosphate, feed grade | 0.5 | 10 |
| Calcium carbonate | 0.5 | 10 |
| Sodium chloride | 0.3 | 6 |
| Trace mineral premix | 0.03 | 0.6 |
| Vitamin A and $D_2$ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin $D_2$ and 385.7 g. of soybean feed with 1% oil added
**Corn distillers dried grains with solubles containing 20,000 I.U. of d-alpha tocopheryl acetate per pound The mixed feed was compressed into pellets. At an average daily ingestion rate of 15 pounds of feed per animal, this feed supplies approximately 300 mg. of A-27106 per animal per day.

EXAMPLE 9

Preparation of Metabolite A-27106 Free Acid

Metabolite A-27106 (100 mg.), prepared in the sodium form by procedures described in Examples 1 and 2, was dissolved in 100 ml. of methanol-water (1:1). The resulting solution was titrated to pH 3 by dropwise addition of 1 N HCl. Methanol was then removed under vacuum.

The resulting solution was extracted twice with chloroform (100 ml. each). The chloroform extract was dried ($MgSO_4$) and evaporated under vacuum to give 85 mg. of the acid form of metabolite A-27106.

EXAMPLE 10

Cesium Salt of Metabolite A-27106

Metabolite A-27106 free acid (97.3 mg.), prepared as described in Example 9, was dissolved in 100 ml. of methanol-water (1:1). The resulting solution was titrated to pH 7.1 by dropwise addition of 1 N cesium hydroxide. methanol was removed under vacuum. This solution was extracted twice with equal volumes of chloroform. The chloroform extract was dried ($MgSO_4$) and evaporated under vacuum to obtain a white amorphous solid. Elemental analysis showed the presence of about 13 percent metal.

EXAMPLE 11

Lithium Salt of Metabolite A-27106

The procedures of Example 10 were repeated, using lithium hydroxide instead of cesium hydroxide. The lithium salt of A-27106 is a white solid exhibiting some organization tending toward crystallinity, but lacking a well-organized X-ray diffraction pattern.

EXAMPLE 12

Ammonium Salt of Metabolite A-27106

The procedures of Example 10, using ammonium hydroxide instead of cesium hydroxide, are employed to produce the ammonium salt of metabolite A-27106. This product has the general properties and utilities of the other forms.

We claim:

1. Metabolite A-27106, or the sodium, lithium, potassium, rubidium cesium or ammonium salt thereof, which metabolite is a white solid having a molecular weight of about 832 and a titratable group with a pKa value of 7.2; and the sodium salt of which is a white crystalline solid, relatively soluble in lower alkanol, but generally insoluble in lower alkane and which has:

a. a molecular weight of 854, as determined by mass spectrometry;
b. an approximate elemental composition of 58.78% carbon, 8.51% hydrogen, 27.85% oxygen, and 3.63% sodium;
c. an empirical formula of $C_{42}H_{71}O_{16}Na$;
d. an infrared absorption spectrum in chloroform as shown in the accompanying drawing;
e. a mass spectrum which shows a molecular-ion peak at m/e 854.44630 and characteristic peaks at m/e 836.44129, 779.44690, 761.44740; and
f. an Rf value of 0.49 on silica-gel thin-layer chromatography in benzene-methanol (7:3).

2. The method of producing the sodium salt of metabolite A-27106 of claim 1 which comprises converting about 0.1 to 1.0 grams per liter of monensin to the sodium salt of metabolite A-27106 with the enzyme system of *Streptomyces candidus* NRRL 5449 in an aqueous culture medium in the presence of an effective amount of glucose until a sufficient amount of metabolite A-27106 is imparted to said medium.

3. The method of claim 2 which includes the additional step of recovering said sodium salt of metabolite A-27106.

* * * * *